United States Patent [19]

Climo et al.

[11] Patent Number: 6,028,051
[45] Date of Patent: Feb. 22, 2000

[54] METHOD FOR THE TREATMENT OF STAPHYLOCOCCAL DISEASE

[75] Inventors: Michael W. Climo; Gordon L. Archer, both of Richmond, Va.; Beth P. Goldstein, Tarrytown, N.Y.

[73] Assignee: Ambi Inc., Tarrytown, N.Y.

[21] Appl. No.: 09/140,732

[22] Filed: Aug. 27, 1998

Related U.S. Application Data

[60] Provisional application No. 60/053,470, Jul. 23, 1997.

[51] Int. Cl.$^7$ .......................... A61K 38/00; A61K 31/70
[52] U.S. Cl. ................................... 514/2; 514/37
[58] Field of Search ............................ 514/2, 37

[56] References Cited

U.S. PATENT DOCUMENTS

| | | | |
|---|---|---|---|
| 3,067,099 | 12/1962 | McCormick et al. | 424/115 |
| 4,931,390 | 6/1990 | Recsei | 435/183 |
| 5,858,962 | 1/1999 | Blackburn et al. | 514/2 |

OTHER PUBLICATIONS

Bramley et al., "Effects of lysostaphin on staphylococcis–aureus inhfections of the mouse mammary gland", Res Vet Sci 49 (1) 1990 p. 120–121 (see the enclosed abstract).

*Primary Examiner*—Kevin E. Weddington
*Attorney, Agent, or Firm*—Long, Aldridge & Norman, LLP; Steven B. Kelber

[57] ABSTRACT

Lysostaphin is an effective antibiotic in the treatment of staphylococcal infection. Large doses of lysostaphin or lysostaphin analogues are effective in short course, or even one dose administrations, in treating and eradicating staphylococcal infections, including those resistant to conventional antibiotics.

17 Claims, No Drawings

METHOD FOR THE TREATMENT OF STAPHYLOCOCCAL DISEASE

RELATED APPLICATIONS

This application is related to pending application, U.S. patent application Ser. No. 09/120,030, filed Jul. 23, 1998, which claims priority of U.S. Provisional Patent Application Ser. No. 60/053,470. The entirety of U.S. Ser. No. 09/120,030 is incorporated herein by reference.

BACKGROUND OF THE INVENTION

1. Field of the Invention

This invention pertains to the administration of lysostaphin for the purpose of treatment of staphylococcus infection in mammals, including humans, as well as pharmaceutical preparations used in said treatment. This invention also pertains to methods of addressing particular disease conditions, including staphylococcal endocarditis; staphylococcal bacteremia; and staphylococcal infection of kidneys, lungs, skin, bone, burns, wounds and prosthetic devices. The invention embraces the use of lysostaphin broadly, including not only wild type lysostaphin but recombinant lysostaphin; lysostaphin variants with amino acid sequences varying from the published 'natural sequence' of the mature peptide (U.S. Pat. No. 4,931,390) due to genetic mutations (such as substitutions, additions, deletions), post-translational processing, or genetic engineering, chimeric fusion proteins and the like; or a combination of these kinds of variations.

2. Background of the Prior Art

Lysostaphin is an enzyme, first identified in *Staphylococcus simulans* (formerly known as *S. staphylolyticus*), which has antimicrobial activity by virtue of its proteolytic activity on glycine-containing bridges in the cell wall peptidoglycan of bacteria (Zygmunt, et al., Progr. Drug Res. 16:309–333 (1972)). In vitro, lysostaphin is particularly active against *Staphylococcus aureus,* because the cell wall bridges of this species contain a high proportion of glycine, although activity against other species of staphylococci has been demonstrated (Ibid.).

The activity of lysostaphin has also been explored in animal infection models. For the purposes of this discussion, the results of intraperitoneal treatment after intraperitoneal infection will not be considered; this experimental design is similar to an in vitro experiment. In intraperitoneal infection models there have been two reports of survival of 50% of treated mice after single or multiple subcutaneous administrations of a total of approximately 1 mg/kg of a lysostaphin preparation (Schuhardt, et al., J. Bacteriol. 88:815–816 (1964); Harrison, et al., Can. J. Microbiol. 13:93–97 (1967)). A total dosage of 6 mg/kg was reported to protect 100% of the mice in one of these studies (Harrison, et al., Ibid.). The virulence of the bacterial challenge used in both studies appears to be quite low, as the untreated infected mice did not all die within a short period of time.

Several experiments used a mouse subacute model measuring the bacterial load in the kidneys after infection with the Giorgio strain of *S. aureus* (Dixon, et al., Yale J. Biol. Med. 41:62–68 (1968); Schaffner, et al., Yale J. Biol. Med. 39:230–244 (1967); Harrison, et al., J. Bacteriol. 93:520–524 (1967)). When a lysostaphin preparation was administered intravenously within 6 hours after infection, significant reductions in the numbers of bacteria in the kidneys were observed with dosages of 1.5 mg/kg or higher. However, established infections were more refractory; only modest reductions in the numbers of bacteria were seen when treatment was withheld for 24 hours or longer, even with dosages of 125 or 250 mg/kg of a lysostaphin preparation. The effect of multiple treatments was not studied.

A single study, (Goldberg, et al., Antimicrob. Ag. Chemother. 1967:45–53 (1967)), employed a limited number of dogs in an unusual endocarditis model. The dog model has not been further developed. The Goldberg, et al., experiment was not comparative, and is therefore of limited utility in assessment of the administration of lysostaphin. However, high dosages of lysostaphin (at least 50 mg/kg/treatment) were only moderately effective, as judged by the health of the dogs and by the extent of reduction in the number of bacteria in the heart valves and kidneys.

Limited human trials were conducted aimed at eradication of nasal carriage of *S. aureus* by topical application of lysostaphin to the nares (Martin, et al., J. Lab. Clin. Med. 70:1–8 (1967); Martin, et al., J. Lab. Clin. Med. 71:791–797 (1968); Quickel, et al., Appl. Microbiol. 22:446–450 (1971)). Nasal carriage is not in itself a disease state. It does constitute a risk factor for infection of patients treated by colonized health care professionals or for self-infection in the case of a colonized patient.

The art reports treatment of one very ill human patient with a single dose of parenterally administered lysostaphin, followed by an antibiotic, gentamicin, three days later. The patient died, but did exhibit a reduction in bacteremia (Stark, et al., N. Engl. J. Med. 291:239–240 (1977)).

Immunogenic phenomena observed during the course of the animal and human studies, were noted as a great concern. Contamination of the lysostaphin preparations with extraneous substances may have been responsible for at least some of these phenomena.

No further development of the enzyme as a therapeutic agent occurred, given the lack of desired effectiveness in the studies discussed. This may have been further due to the difficulty in producing and purifying lysostaphin.

The staphylococcal gene for lysostaphin has been sequenced and cloned (U.S. Pat. No. 4,931,390). Lysostaphin for use as a laboratory reagent has been produced by fermentation of a non-pathogenic recombinant strain of *Bacillus sphaericus,* from which it is readily purified.

Although this previous art did not teach that lysostaphin is highly effective in clearing established infections from various organs in animal models, more recently it has been demonstrated that a regimen of multiple, relatively low, doses of lysostaphin was surprisingly effective in curing experimental endocarditis in rabbits caused by methicillin-resistant *Staphylococcus aureus* (MRSA) or vancomycin intermediate susceptible *S. aureus* (VISA)(U.S. patent application Ser. No. 09/120,030, filed Jul. 21, 1998; Climo, et al., Antimicrob. Agents Chemother. 42:1355–1360 (1998).) The good tolerability of lysostaphin in the rabbit model suggests that a multiple dose regimen of lysostaphin, alone or in combination with other antibiotics, may be practicable in treating human disease. However, it remains an object of those of skill in the art to develop the most tolerable and most effective means of using lysostaphin to treat human staphylococcal disease.

Conventional administration of antibiotics typically involves an extended course of low to medium level dosage. Particularly resistant infections, such as osteomyelitis may require treatment over many weeks, or even months. Other staphylococcal infections may be treated in a shorter time period, but nonetheless, typically extend over 10–14 days. In severe infections, that present extreme life-threatening conditions, such as endocarditis, even the most aggressive antibiotic therapy typically contemplates a period of administration of at least several weeks.

Before the infection is completely cleared, organ damage often results from infections with highly virulent bacteria, such as *S. aureus*. Additionally, staphylococcal infections, particularly with *S. aureus*, can evolve from an initial, relatively benign infection (such as low-grade bacteremia or skin infection) to a deep-seated single or multiple organ infection, including endocarditis. These events may occur despite using the best available antibiotics, because antibiotic action is not rapid enough.

Furthermore, it is known that even the safest drugs can have undesired side effects. Although lysostaphin has thus far not been shown to have adverse effects in animal models, other protein drugs are known to cause immunogenic reactions in humans after prolonged treatment. It is also possible that prolonged treatment will induce the production of neutralizing antibodies, which would progressively reduce the effectiveness of the protein therapeutic.

Accordingly, it remains an object of those of ordinary skill in the art to provide an effective treatment regimen that effectively eradicates even significant, established staphylococcal infections and prevents the development of serious infections, that contemplates administration over a very short period.

SUMMARY OF THE INVENTION

The above objects, and other objects that will become more apparent through the disclosure set forth below, are achieved by the administration of relatively high dosages of lysostaphin, of at least 50, preferably 100, mg/kg. (As used herein, mg/kg refers to milligrams of lysostaphin analogue per kilogram of body weight administered in any 24-hours period). These unprecedented high dosages can include "single dose treatments", where effective protection is provided by a single large dose of lysostaphin, as well as "short course administration", or "repeated dose administration". In short course administration, the relatively high dosage, which may not be as high as the single dose administration, but is still on the order of 50–100 mg/kg or greater, is repeated, daily, for a period of 2–5 days. Repeated dose administration includes a first dose, followed by one or two repeats of that dosage, separated by perhaps at least a day. Thus, a dose of lysostaphin of 100 mg/kg or greater on day 1, day 3 and day 5 or other pattern with greater separation between doses of administration may also be effective in eradicating staphylococcal infections.

The administration of single or short course, relatively high, dosages of lysostaphin (50–100 mg/kg or greater) is a dramatically effective therapy for the treatment of staphylococcal infections, particularly infections that are resistant to treatment, and/or typically associated with significant morbidity and mortality. Further, administered in this way, lysostaphin is demonstrated to be effective against staphylococcal bacteria that are at least partially resistant to available antimicrobial agents, such as beta-lactam antibiotics including penicillinase-stable penicillins, vancomycin, etc.

The invention further includes combinatorial therapies, calling for a single or short course high dose of lysostaphin, which may be administered before or after initiation of other therapies, and may be followed by two or more days of treatment with one or more other antimicrobial agents; this treatment regimen may be repeated by giving one or more additional high dosages of lysostaphin, at intervals of two to 10 days, in the presence or absence of continuing therapy with other antimicrobial agents. Particularly preferred antibiotics for administration in concert with lysostaphin according to this invention are rifamycins (isolated from microorganisms or synthetically or semi-synthetically produced, such as rifampin) and glycopeptides (a group of molecules, among which the naturally occurring molecules usually contain a heptapeptide and one or more sugar moieties), whether naturally produced and isolated or semi-synthetic preparations including vancomycin, teicoplanin), etc.

The availability of cloned, recombinant and variant lysostaphin further expands this invention. Related enzymes have been identified, and can further be used together with, or in place of, lysostaphin.

The cloning and sequencing of the lysostaphin gene permits the isolation of variant enzymes that can have properties similar to or different from those of wild type lysostaphin. One such altered enzyme, bearing a single amino acid change, has been characterized and shown to have potent anti-staphylococcal activity in vitro and in an animal infection model (U.S. patent application Ser. No. 09/120,030, filed Jul. 21, 1998).

Recently, another glycylglycine endopeptidase (ALE-1, from *Staphylococcus capitis* EPK1) has been described. ALE-1 is distinct from lysostaphin, although the two enzymes have considerable amino acid homology (Sugai et al., J. Bacteriol. 179:1193–1202(1997)). Another peptidoglycan hydrolase with a lower degree of homology to lysostaphin, but which also possesses endopeptidase activity, is zoocin A, produced by *Streptococcus zooepidemicus* 4881 (Simmonds et al., Applied and Environmental Microbiology 62:4536–4541 (1996); Simmonds et al., Gene 189:255–261(1997)). Other lysostaphin analogues, including naturally occurring enzymes of this type, or even chimeric enzymes obtained by fusing the binding domain of one enzyme to the catalytic domain of another, will be potent agents capable of addressing difficult to treat bacterial diseases caused by staphylococci or other pathogenic bacteria.

Definitions

Terms used in this application are used, where possible, in the sense of their normal and typical usage. Certain terms are used to describe a class of actions or compounds, to provide a generic description of items or scientific phenomena that are logically grouped together.

Lysostaphin Analogue

Any enzyme, including lysostaphin (wild type), any lysostaphin mutant or variant, any recombinant, or related enzyme that retains the proteolytic ability, in vitro and in vivo, of proteolytic attack against glycine-containing bridges in the cell wall peptidoglycan of staphylococci. Variants may be generated by post-translational processing of the protein (either by enzymes present in a producer strain or by means of enzymes or reagents introduced at any stage of the process) or by mutation of the structural gene. Mutations may include site-deletion, insertion, domain removal and replacement mutations. The lysostaphin analogues contemplated in the instant invention may be recombinantly expressed or otherwise.

Parenteral

Administration by injection, including intravenous, intramuscular, subcutaneous, intraorbital, intraspinal, intraperitoneal and by direct perfusion or delivery to organs or tissues through injection (e.g., intramedullary). Administration by inhalation is also contemplated as part of this invention.

DETAILED DESCRIPTION OF THE INVENTION

*Staphylococcus aureus* is a highly virulent human pathogen. It is the cause of a variety of human diseases, ranging from localized skin infections to life-threatening bacteremia and infections of vital organs. If not rapidly controlled, a *S. aureus* infection can spread rapidly from the initial site of infection to other organs. Although the foci of infection may not be obvious, organs particularly susceptible to infection include the heart valves, kidneys, lungs, bones, meninges and the skin in burn patients. Surgical or traumatic wounds, and any region in which a foreign body is present are also frequently infected. These infections, which may arise in the community or during a hospital stay, are a cause of significant morbidity and mortality, which may be as high as 60% in severe infections in certain populations, even when the best available treatment is used. Other species of staphylococci (coagulase-negative staphylococci such as *S. epidermidis*) are less virulent, but can colonize catheters or prosthetic devices; this can have devastating consequences, for example when the device is an implanted heart valve.

Resistance to available antimicrobial agents appears to emerge particularly easily in staphylococci, starting with penicillin resistance in *S. aureus*, which emerged soon after the dawn of the antibiotic era. Virtually all staphylococcal infections, whether arising in the community or the hospital, are no longer susceptible to first-generation penicillins due to the production of penicillinase; strains that are also resistant to penicillinase-stable penicillins (such as methicillin) are also now a significant problem, particularly in hospital-acquired infections. (Centers for Disease Control and Prevention, 1997. Reduced susceptibility of *Staphylococcus aureus* to vancomycin—Japan, 1996. Morbidity and Mortality Weekly Report 1997;46:624–626.)

Vancomycin has become the first-line treatment for methicillin-resistant staphylococcal infection, particularly in hospitals. However, as is evident from the high mortality rates, no currently available treatment is ideal for certain diseases, such as *S. aureus* endocarditis and bacteremia, which require rapid reduction in numbers of bacteria in order to prevent irreversible damage to the heart and to the other organs to which infection often spreads via the bloodstream. One reason for failure of currently available therapies is that they act relatively slowly, particularly in vivo, where rapid sterilization of infected sites may be required for complete and rapid recovery of the patient. In such a life-threatening situation, and in some other infections (for example in which treatment regimens are very lengthy, such as osteomyelitis), novel therapies or new combinations of therapies may greatly improve patient outcome.

While studying the tolerability of high dosages of lysostaphin in infected rabbits, it was discovered that single, high dosages were surprisingly efficacious in curing infections. This is demonstrated, below, in a very severe well-characterized animal infection model, endocarditis in the rabbit caused by strains of *S. aureus* that are methicillin-resistant (MRSA) and are also vancomycin intermediate susceptible *S. aureus* (VISA). In particular, we demonstrate complete sterilization of the heart valve vegetations and kidneys in most of the animals.

While certain immunologic side-effects observed in much earlier studies may give concern in some, but not other situations (such as emergency or short term situations) suitably pure preparations of lysostaphin analogues, obtained by the fermentation of harmless recombinant strains of bacteria, are expected to be less prone to induce immunogenic or other side-effects. Additionally, restriction of the number of doses administered would be expected to reduce the risk of immunological response to a protein therapeutic.

Effective pharmaceutical formulations of these antimicrobial enzymes include aqueous solutions or dry preparations (e.g., lyophilized, crystalline or amorphous, with or without additional solutes for osmotic balance) for reconstitution with liquids, suitable for parenteral delivery of the active agent, preferably via intravenous (i.v.), intramuscular (i.m.), subcutaneous (s.c.), or intraperitoneal (i.p.) routes or intrathecally or by inhalation or by direct instillation into an infected site so as to permit blood and tissue levels in excess of the minimal inhibitory concentration (MIC) of the active agent to be attained and thus to effect a reduction in bacterial titers in order to cure or to alleviate an infection. Furthermore, the active lysostaphin analogue can be coadministered, at the same time or consecutively, with other antimicrobial agents so as to more effectively treat an infectious disease. Formulations may be in, or be reconstituted in, small volumes of liquid suitable for bolus i.v. or peripheral injection or by addition to a larger volume i.v. drip solution, or may be in, or reconstituted in, a larger volume to be administered by slow i.v. infusion.

Suitable dosages and regimens of lysostaphin may vary with the severity of the infection and the sensitivity of the infecting organism. Dosages may range from 50 to 2000 mg/kg, preferably from 100 to 500 mg/kg, given as a single or divided dose or as a continuous infusion during a 24-hour period, repeated if necessary one or more times at intervals of 2 to 14 days, preferably at intervals of 5 to 10 days.

EXAMPLES

All experiments were conducted using lysostaphin or a variant enzyme produced by fermentation of recombinant *B. sphaericus* strains engineered to contain the lysostaphin gene described by Recsei (U.S. Pat. No. 4,931,390) or a mutant thereof. Specifically, the lysostaphin analogues prepared by fermentation of *B. sphaericus* varies from the published sequence by having as many as 2 fewer or up to 2 additional amino acids at the N-terminus. In particular, the data herein are largely derived from studies using preparations of lysostaphin analogues wherein the majority component is one that lacks the two N-terminal amino acids of the published sequence. However, the findings are not limited to this preparation. Similar results may be obtained with any preparation having suitable purity and activity.

Example 1
In Vitro Activity of Lysostaphin Against VISA

Prior to conducting infection model studies in animals, the minimal inhibitory activity (MIC) of lysostaphin for VISA strains, including two U.S. and one Japanese clinical isolate and a laboratory mutant, was determined to be 0.015–0.03 μg/ml. Standard broth microdilution methods were used (National Committee for Clinical Laboratory Standards, 1993. Approved Standard M7-A3. Methods for dilution antimicrobial susceptibility tests for bacteria that grow aerobically—Third edition. National Committee for Clinical Laboratory Standards, Villanova, Pa.), with the addition of 0.1% (wt/vol) bovine serum albumin to prevent adsorption of lysostaphin to plastic pipettes and microtiter trays. The MIC of vancomycin for these strains is 8 μg/ml, twice the generally accepted cutoff for complete susceptibility to this antibiotic (National Committee for Clinical Laboratory Standards, 1993. Approved Standard M2-A5. Performance standards for antimicrobial disk susceptibility tests—Fifth edition. National Committee for Clinical Laboratory Standards, Villanova, Pa.).

Example 2
Efficacy of Single High Doses of Lysostaphin Against Experimental *S. aureus* Endocarditis in Rabbits Aortic valve endocarditis was established in New Zealand white rabbits weighing approximately 3 kg. Rabbits were anaesthetized and the right carotid artery surgically exposed and cannulated with a polyethylene catheter which was advanced into the left ventricle of the heart. After at least 24 h, the rabbits were infected intravenously with $10^6$–$10^7$ cells of MRSA VISA strain HP5827 (Michigan strain) or with $10^6$–$10^7$ cells of MRSA VISA strain Mu-50 (Japanese strain). Twenty-four hours later, the animals were randomly assigned to different treatment groups: untreated control; positive control, vancomycin 30 mg/kg twice daily for 3 days; lysostaphin 30 mg/kg twice daily for 3 days; lysostaphin 100 mg/kg once; lysostaphin 250 mg/kg once; lysostaphin 500 mg/kg once. Any rabbits whose infection was not confirmed by pre-treatment blood culture were eliminated. In addition, all rabbits included in the analysis were confirmed at autopsy to have had an established endocarditis infection, as judged by the presence of an aortic vegetation indicative of an ongoing or a previously existing disease state. All treatments were intravenous; the single high doses of lysostaphin were administered over 30 minutes, using an infusion pump. The state of health of the rabbits was assessed at intervals. From the rabbits treated with a single high dose of lysostaphin, blood samples were withdrawn for culture of bacteria during days 1, 2, and 3 (start of treatment is day 1). All of the rabbits were sacrificed on the fourth day after beginning treatment (18 hours after the last treatment for multiple dose regimens, 72 hours after treatment in the case of single doses). Aortic vegetations were removed and weighed and processed to determine the number of viable bacteria, expressed as $\log_{10}$CFU/gram. The limit of detection is $10^2$ CFU/gram ($\log_{10}$CFU/gram=2.0). The kidneys, in which infected abscesses develop, were also homogenized to determine the number of viable bacteria. The mean titers of bacteria per gram of tissue were compared by the Bonferroni t-test. Comparison of the rates of sterilization were made using Fisher's exact test. Statistical significance was defined as a P value of $\leq 0.05$.

As shown in table 1, vancomycin (the standard treatment for MRSA infection in humans) was essentially ineffective against HP5827 (which is a VISA strain). The vancomycin regimen used, 30 mg/kg intravenously twice daily for 3 days, is the standard regimen and is active against non-VISA MRSA strains in this infection model (U.S. patent application Ser. No. 09/120,030, filed Jul. 21, 1998; Climo, et al., Ibid.). Lysostaphin at the same dosage was highly efficacious in reducing the bacterial count in the heart valve vegetations and also in the kidneys, and was furthermore able to completely eradicate bacteria from the heart valves in 5 out of 6 rabbits and from the kidneys in 4 out of 6 rabbits. These results were not unexpected, as similar data were generated previously using a laboratory-derived mutant VISA strain. However, the present data confirm that lysostaphin is equally active against clinical VISA isolates in the rabbit infection model. (The same is not true for vancomycin, which had somewhat better activity against the laboratory VISA strain (Ibid.).) Results with another clinical VISA isolate, from Japan, are similar to the above (Table 2).

As part of the evaluation of the tolerability of lysostaphin in mammals, several rabbits infected with VISA strain HP5827 were treated intravenously once with higher dosages of lysostaphin, ranging from 100 to 500 mg/kg. Since all of these rabbits tolerated the lysostaphin, they were kept and monitored and later sacrificed for evaluation of bacterial counts in the heart valves and kidneys.

Blood was withdrawn on days 1, 2 and 3 (day one is the treatment day) and plated on Mueller-Hinton agar to detect bacteria. In all cases, the blood cultures were sterile (limit of detection 10 viable cells per ml). This is a surprising result, because previous experiments with single dosages of 60 mg/kg vancomycin or 15 mg/kg lysostaphin produced only a transient drop in bacteremia, with viable cells detected again in the blood by 24 hours after treatment (Climo, et al., Ibid.).

Furthermore, as shown in Table 1, in 4 rabbits treated with a single dose of 100 mg/kg of lysostaphin, at sacrifice (on day 4) the mean bacterial count in the heart valve vegetations was reduced to about the same extent as in rabbits that received three days of twice daily treatment with 30 mg/kg lysostaphin (total dose 180 mg/kg) and, significantly, two of the four rabbits had completely sterile valves (less than $\log_{10}=2$ bacteria per gram). Additionally, all 4 rabbits treated once with 100 mg/kg lysostaphin had no bacteria detectable in the kidneys.

One rabbit each was treated with of the single doses of 250 and 500 mg/kg lysostaphin, respectively. Both of these animals had completely sterile heart valve vegetations and kidneys.

TABLE 1

Efficacy of different lysostaphin treatment regimens against *S. aureus* endocarditis in rabbits (VISA strain HP5827)

| Treatment | Mean $\log_{10}$CFU/gram ± SD* | | Number sterile/total animals treated | |
|---|---|---|---|---|
| | heart valve vegetation | kidney | heart valve vegetation | kidney |
| Untreated control | 10.3 ± 0.51 | 7.46 ± 0.6 | 0/11 | 0/11 |
| Vancomycin 30 mg/kg twice a day | 9.66 ± 1.1 | 3.14 ± 1.39 | 0/9 | 0/9 |
| Lysostaphin 30 mg/kg twice a day | 2.03 ± 0.06[a] | 2.09 ± 2.2 | 5/6[a] | 4/6[a] |
| Lysostaphin 100 mg/kg once on day 1 | 2.29 ± 033[a] | ≤1.0[a] | 2/4 | 4/4[a] |
| Lysostaphin 250 mg/kg once on day 1 | ≤2.0 | ≤1.0 | 1/1 | 1/1 |
| Lysostaphin 500 mg/kg once on day 1 | ≤2.0 | ≤1.0 | 1/1 | 1/1 |

*SD: standard deviation of the mean
[a] $p < 0.05$ as compared with untreated control and vancomycin groups

TABLE 2

Efficacy of lysostaphin against *S. aureus* endocarditis in rabbits (VISA strain MU-50)

| Treatment | Mean $\log_{10}$CFU/gram of vegetation | no. sterile/total treated |
|---|---|---|
| Untreated control | 10.4 | 0/4 |
| Vancomycin 30 mg/kg twice a day | 9.8 | 0/4 |
| Lysostaphin 30 mg/kg twice a day | 2.5 | 1/2 |

These results could not have been anticipated on the basis of previous studies. In particular, rapid sterilization of the blood that persists for 3 days after a single treatment has never been seen or reported before with any antimicrobial agent in this infection model. Additionally, complete sterilization of the kidneys of all 6 rabbits, and of the heart valve vegetations of 4 of the 6 rabbits, treated with single doses of 100, 250 or 500 mg/kg lysostaphin is unprecedented. The rapid action of a single high dose of lysostaphin in vivo suggests that short or intermittent regimens of antimicrobial lysostaphin enzyme or analogues could greatly improve the outcome in patients with serious staphylococcal infections that require rapid reduction in bacterial load.

The above data demonstrate the efficacy of lysostaphin against *S. aureus* that are both MRSA (methicillin-resistant) and vancomycin intermediate susceptible (VISA). These organisms are a newly emerging problem.

The rabbit endocarditis model is now very well standardized and is accepted as a rigorous test of the ability of antimicrobial agents to cure severe human infections. Previous work with lysostaphin in the rabbit endocarditis model demonstrated the efficacy of lysostaphin against infections caused by multiply antibiotic-resistant *S. aureus*, when the lysostaphin was administered in traditional multiple dose, multiple day treatment regimens with or without another antibiotic such as vancomycin. Earlier work with a dog endocarditis model failed to show consistent results with single or multiple treatments as high as 50 to 250 mg/kg/treatment (Goldberg, et al., Antimicrob. Ag. Chemother. 1967:45–53 (1967)).

The results presented herein demonstrate not only the unexpected effectiveness of a single high dose of lysostaphin against *S. aureus* endocarditis, but show that such efficacy is far superior to that expected for standard treatments. Currently available treatments are often not effective in dealing with life-threatening infections that may lead to irreversible tissue damage and that therefore require rapid reduction in bacterial numbers to prevent such damage as well as metastatic spread of infection to other vital organs. The above results indicate that one or a few treatments with high doses of lysostaphin analogues, alone or in combination with standard dosage regimens of other agents, have the potential for effectiveness in the treatment of such infections. Furthermore, based on the in vitro activity of lysostaphin against staphylococci (U.S. patent application Ser. No. 09/120,030, filed Jul. 21, 1998), and on the fact that very high doses of lysostaphin are well tolerated by rabbits, it is to be expected that lysostaphin analogues, alone or in combination with other agents, will also be useful against species of staphylococci other than *S. aureus*. Among the agents suitable for use together with lysostaphin are vancomycin and other glycopeptides, rifampin and other rifamycins, and other anti-infective agents that have activity against staphylococci.

Lysostaphin analogues may be used not only in the treatment of staphylococcal endocarditis but other potentially lethal staphylococcal diseases, such as bacteremia and infections of other vital organs, such as kidneys, lung, skin and bone. The instant methods are also applicable to the treatment of infections of burns, wounds and prosthetic devices. These same methods may be used, in particular, in treatment of diseases such as osteomyelitis, which result from an infection of a type or severity requiring prolonged treatment with currently used antimicrobial agents. The instant invention further extends to the use of lysostaphin analogues in treating such infections and diseases when they are caused by staphylococci that are resistant to routinely used antibiotics.

The invention of this application has been described in generic terms, by specific identification and by exemplification. The invention is not limited to the individual species identified nor should the examples be construed as limiting. A wide variety of lysostaphin analogues can be used in the practice of this invention, as can combinatorial agents. Such variations, as well as variations in the method of administration, and other variations that will occur to those of ordinary skill in the art without the exercise of inventive faculty, remain within the scope of the invention, unless excluded by the recitations of the claims set forth below.

What is claimed is:

1. A method of treating staphylococcal infection in a patient, comprising:

administering to said patient a single dose of lysostaphin analogue in a dosage of at least 50 mg lysostaphin/kg body weight (mg/kg), wherein said administration is not continued, and said infection is reduced, and wherein said infection is one selected from the group consisting of endocarditis, bacteremia, kidney infection, lung infection, skin infection, bone infection, burn infection, wound infection, infection of prosthetic devices and a combination thereof.

2. The method of claim 1, wherein said infection is eradicated.

3. The method of claim 1, wherein said dosage is 100 mg/kg–2,000 mg/kg.

4. The method of claim 1, wherein said patient is a human.

5. The method of claim 1, wherein said method further comprises administering a second antibiotic effective in treating said staphylococcal infection.

6. A method of treating staphylococcal infection in a patient, comprising:

administering to said patient an effective amount of lysostaphin analogue in a dosage of at least 50 mg/kg/day, wherein said administration is continued for a period of 1–5 days, and said infection is reduced, and wherein said infection is one selected from the group consisting of endocarditis, bacteremia, kidney infection, lung infection, skin infection, bone infection, burn infection, wound infection, infection of prosthetic devices and a combination thereof.

7. The method of claim 6, wherein said infection is eradicated.

8. The method of claim 6, wherein said dosage is 100 mg/kg–2,000 mg/kg.

9. The method of claim 6, wherein said patient is a human.

10. The method of claim 6, wherein said method further comprises administering a second antibiotic effective in treating said staphylococcal infection.

11. A method of treating staphylococcal infection in a patient, comprising:

administering to said patient an amount of lysostaphin analogue in a dosage level of at least 50 mg/kg on a first day of treatment, and repeating said administration once or twice, wherein each said repetition is separated by at least one day on which lysostaphin is not administered, and said infection is reduced, and wherein said infection is one selected from the group consisting of endocarditis, bacteremia, kidney infection, lung infection, skin infection, bone infection, burn infection, wound infection, infection of prosthetic devices and a combination thereof.

12. The method of claim 11, wherein said infection is eradicated.

13. The method of claim 11, wherein said dosage is 100 mg/kg–2,000 mg/kg.

14. The method of claim 11, wherein said patient is a human.

15. The method of claim 11, wherein said method further comprises administering a second antibiotic effective in treating said staphylococcal infection.

16. A composition of matter, comprising a single dosage formulation of lysostaphin effective in treating staphylococcal infection in a patient wherein said single dosage composition comprises at least 2,200 mg lysostaphin analogue, and a pharmaceutically acceptable carrier.

17. The composition of claim 16, wherein said composition comprises, in addition to said lysostaphin analogue, an additional antibiotic agent.

* * * * *